United States Patent [19]

O'Murchú

[11] 3,984,434

[45] Oct. 5, 1976

[54] PROCESS FOR THE PRODUCTION OF INDOLE

[75] Inventor: Colm O'Murchú, Visp, Switzerland

[73] Assignee: Lonza Ltd., Gampel, Valais, Switzerland

[22] Filed: Sept. 12, 1974

[21] Appl. No.: 505,517

[30] Foreign Application Priority Data
Sept. 12, 1973 Switzerland.................... 13091/73

[52] U.S. Cl. ............................................. 260/319.1
[51] Int. Cl.² ..................................... C07D 209/58
[58] Field of Search ................................ 260/319.1

[56] References Cited
UNITED STATES PATENTS 2,409,676 10/1946 Gresham et al................ 260/319.1
3,824,252 7/1974 Mauri et al..................... 260/319.1
3,847,937 11/1974 Moggi et al..................... 260/319.1

FOREIGN PATENTS OR APPLICATIONS 684,736 4/1964 Canada............................ 260/319.1

Primary Examiner—Dale R. Ore
Attorney, Agent, or Firm—Christen & Sabol

[57] ABSTRACT

This process involves the production of indole by catalytic dehydrocyclization. The process includes reacting, without the addition of free oxygen and/or a gas containing free oxygen, reacting o-ethylaniline and/or o-aminostyrene with steam in the presence of a particular catalyst. The catalyst contains at least one alkali compound and/or at least one alkaline earth compound and/or at least one compound containing iron, cobalt, chromium, vanadium, titanium, zinc, copper and/or zirconium.

39 Claims, No Drawings

PROCESS FOR THE PRODUCTION OF INDOLE

BACKGROUND OF THE INVENTION

1. Field of This Invention

This invention relates to a process for the production of indole by catalytic dehydrocyclization.

2. Prior Art

It has been proposed in case of dehydrocyclization processes, especially for the production of indole from o-ethylaniline, to use cobalt molybdates, platinum or palladium on an activated aluminum oxide carrier as the catalysts. Such a process, however, has the disadvantage that the catalyst is very expensive and is very quickly deactivated because of formation of large quantities of coke (as a result of which frequent regenerations are required).

In German Pat. application No. 2,049,752 opened to public inspection, a process for the oxydative catalytic dehydrocyclization of subtituted aromatic compounds with free oxygen or a gas containing free oxygen in the presence of a catalyst is described. The catalyst contains one or more oxides and/or anhydrides and/or their compounds. According to such a process, however, larger quantities of CO and $CO_2$ develop along with the desired products, and the addition of air or oxygen and steam results in relatively small space-time yields.

BROAD DESCRIPTION OF THIS INVENTION

An object of this invention is to obtain a process which results in relatively large space-time yields, wherein by-products do not develop (that have to be removed) and wherein the catalyst does not have to be regenerated.

This invention involves a process of achieving that and the other advantages and objects of this invention. The process includes reacting o-ethylaniline and/or o-aminostyrene, without addition of free oxygen or a gas containing free oxygen, with steam in the presence of a particular catalyst. The catalyst contains at least one alkali metal compound and/or at least one alkaline earth metal compound and/or at least one oxide and/or anhydride and/or compounds of the elements iron, cobalt, chromium, vanadium, titanium, zinc, copper and zirconium.

DETAILED DESCRIPTION OF THIS INVENTION

The catalyst preferably contains a potassium compound as the alkali metal compound or preferably contains a barium compound as the alkaline earth metal compound. The alkali metal or alkaline earth metal compounds are usually oxides, carbonates or hydroxides. The alkali metal can be lithium, sodium, potassium, Rb, Cs or Fr. The alkaline earth metal can be Be, Mg, calcium, Sr, barium or Ra.

Examples of catalyst which are useful in this invention are: $Fe_2O_3$—$K_2CO_3$—$Cr_2O_3$—$V_2O_5$, 74.5:20:2:3.5 percent; $Fe_2O_3$—$K_2CO_3$—$Cr_2O_3$—$CO_3O_4$—Portland cement, 46.3:26.2:2.5:5.0:20.0 percent; $Fe_2O_3$—$K_2CO_3$—$Cr_2O_3$—CuO-Portland cement, 43.9:25.0:2.5:4.8:23.8 percent; $Cr_2O_3$—$Al_2O_3$—KOH, 19:79:2 percent; $Cr_2O_3$—$K_2CO_3$, 93:7 percent; ZnO—$Cr_2O_3$—$BaCrO_4$—Portland cement, 35.8:29.0:17.7:17.5 percent; $TiO_2$—$Cr_2O_3$—$K_2CO_3$, 80:4:16; $TiO_2$—$Cr_2O_3$—$V_2O_5$—$Cr_2O_3$, 76.4:16.8:2.6:4.2 percent; $(ZrO_2$—$Al_2O_3)$—BaO, 95:5; $(ZrO_2$—$Al_2O_3)$ —$K_2CO_3$—KOH, 90:9:1 percent; copper chromite stabilized and activated with barium oxide; and $K_2CO_3$ activated with iron oxide (containing K compounds).

The catalyst can be used either in a stationary bed, as well as in a moving bed or in a fluidized bed. The catalyst practically does not lose its effectiveness and its activity is completely preserved even with extensive and continued usage. Therefore, no reactivation of the catalyst is necessary.

Additionally an inert diluent gas can be used. The inert diluent gas can be nitrogen, argon, carbon dioxide, saturated hydrocarbons, such as, for example, n-pentane, isopentane, n-hexane or n-heptane, or any other kind of inert substance (i.e., which is not changed under the reaction conditions).

The mole ratio of steam to the aromatic starting reactant or reactants can vary between 3:1 and 75:1.

The process of this invention is carried out at a temperature between 500° and 700°C. and preferably between 550° and 650°C. The reaction pressure can be varied between 10 mm Hg and 10 atmospheres. The process is preferably conducted at atmospheric pressure.

The apparent contact time between the reaction participants and the catalyst is between 0.1 and 60 seconds — the range of 0.5 to 30 seconds is particularly preferred. Apparent contact time between the reaction participants and the catalyst means the ratio between the volume of the catalyst bed and flow of the reaction participants (as gas) under the reaction conditions. O-aminostyrene or 1-amino-2-vinylbenzene is:

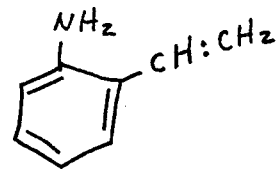

O-ethylaniline or o-aminoethylbenzene is:

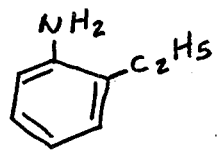

Indole or 2,3-benzopyrrole is:

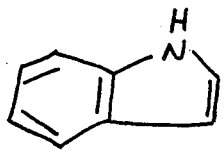

Indole can be used in perfumery.

According to the invention, the reaction can be conducted such that the aminostyrene formed during the reaction is separated by distillation from the reaction product mixture and is admixed with the starting reactant(s) introduced into the reactor.

Preferably the reaction is started with o-ethylaniline and aminostyrene. The o-aminostyrene formed during the reaction as well as the unreacted o-ethylaniline are separated by distillation from the reaction product mixture, and are recycled and added to the fresh o-ethylaniline which is being fed continuously into the reactor.

The following examples explain the invention in more detail. The terms conversion, selectively and yield concepts are defined as follows:

$$\text{Conversion} = \frac{\text{moles of reacted organic compound}}{\text{moles of fed-in organic compound}} \times 100$$

$$\text{Selectivity} = \frac{\text{moles of product obtained}}{\text{moles of reacted organic compound}} \times 100$$

$$\text{Yield} = \frac{\text{moles of compound obtained}}{\text{moles of fed-in organic compound}} \times 100$$

As used in the examples and elsewhere in this application, all percentages, parts, ratios and proportions are on a weight basis unless otherwise stated or obvious to one ordinarily skilled in the art.

EXAMPLE 1

A mixture of gaseous o-ethylaniline and steam, using various catalyst of this invention, was allowed to react under variable conditions (set out in Table 1) in a tubular reactor having an internal diameter of 43 mm and which was electrically heated. The results are given in Table 1.

EXAMPLE 2 o-Ethylaniline at a liquid hourly space velocity of the educt (effluent) of 0.15 per hour was allowed to react at 580°C in the presence of steam and a gas (inert diluent) with a catalyst. The catalyst consisted of copper chromite activated by barium oxide. The molar ratio of water and o-ethylaniline was 16:1. The use of inert diluent gas additives showed no great influence on the results — see Table 2.

Table 2

| Inert Diluent Gas | Molar Ratio of Inert Diluent Gas to o-ethylaniline | Conversion, % | Selectivity, % | |
|---|---|---|---|---|
| | | | Indole | o-ethylstyrene |
| None | — | 37.6 | 50 | 34.6 |
| $N_2$ | 1:1 | 36.5 | 48 | 34.4 |
| Argon | 1:1 | 36.3 | 48 | 33.9 |

EXAMPLE 3 o-Ethylaniline and water were reacted using a catalyst which was copper chromite which was activated with barium oxide. The ratio water to o-ethylaniline was 15:1 and the contact time was 5 seconds. The results for the various temperatures used are shown in Table 3.

Table 3

| Temperature, °C. | Conversion, % | Selectivity, % | |
|---|---|---|---|
| | | Indole | o-aminostyrene |
| 570 | 43.3 | 49.1 | 36.1 |
| 580 | 48.0 | 55.8 | 29.0 |
| 590 | 57.4 | 61.0 | 20.8 |
| 600 | 59.8 | 63.5 | 18.4 |

EXAMPLE 4 o-Ethylaniline and water at a molar ratio of 1:10 were reacted at 570°C using a catalyst comprised of $Fe_2O$-

Table 1

| Catalyst, Percent by Weight | LHSV | Molar Ratio of $H_2O$ to o-ethylaniline | Temperature, °C. | Conversion, % | Selectivity, % | |
|---|---|---|---|---|---|---|
| | | | | | Indole | o-aminostyrene |
| Copper chromite activated with BaO | 0.15 | 15:1 | 580 | 53.5 | 58.5 | 31.2 |
| Copper chromite activated with BaO | 0.058 | 10:1 | 590 | 64 | 69.2 | 15.1 |
| Copper chromite activated with BaO | 0.54 | 10:1 | 600 | 47.5 | 30.9 | 42.5 |
| Activated iron oxide | 0.31 | 15:1 | 570 | 43.8 | 42.6 | 45.1 |
| Activated iron oxide | 0.41 | 18.5:1 | 610 | 54 | 37.5 | 40.5 |
| Activated iron oxide | 0.56 | 16:1 | 575 | 44 | 28.5 | 48.0 |
| $Fe_2O_3$- $K_2CO_3$- $Cr_2O_3$- $V_2O_5$, 74.5:20:2:3.5 percent | 0.41 | 18.5:1 | 610 | 49.5 | 41.1 | 36.2 |
| $Fe_2O_3$- $K_2CO_3$- $Cr_2O_3Co_3O_4$-cement, 46.3:26.2:2.5:5.0:20.0 percent | 0.41 | 18.5:1 | 610 | 45.2 | 34.9 | 48.7 |
| $Fe_2O_3$- $K_2CO_3$- $Cr_2O_3$—CuO-cement, 43.9:25:2.5:4.8:23.8 percent | 0.24 | 25:1 | 600 | 56 | 50.6 | 33.8 |
| $CrO_3$- $Al_2O_3$- KOH, 7.6:90.4:2.0 percent | 0.15 | 15:1 | 580 | 70 | 53.6 | 26.4 |
| $Cr_2O_3$- $K_2CO_3$, 93:7 percent | 0.31 | 10:1 | 590 | 40 | 22.0 | 49.1 |
| Zinc chromite (74 percent ZnO, 23 percent $CrO_3$) + 9 percent $K_2CO_3$ and 1 percent KOH | 0.15 | 15:1 | 570 | 40.4 | 28.0 | 43.8 |
| ZnO- $Cr_2O_3$- BaO-cement, 35.8:29.0:17.7:17.5 percent | 0.042 | 15:1 | 590 | 64 | 67.9 | 13.6 |
| $TiO_2$- $Cr_2O_3$- $K_2CO_3$, 80:4:16 percent | 0.29 | 15:1 | 620 | 38.4 | 25.4 | 29.4 |
| $TiO_2Cr_2O_3$- $V_2O_5$- $K_2CO_3$ 76.4:4.2:2.6:16.8 percent | 0.15 | 15:1 | 580 | 29.8 | 23.9 | 64.4 |
| 98% $ZrO_2$-2% $Al_2O_3$ + BaO, 95:5 percent | 0.15 | 16.5:1 | 580 | 43 | 39.5 | 41.5 |
| 98% $ZrO_2$-2% $Al_2O_3$ + 9% $K_2CO_3$ + 1% KOH | 0.75 | 15:1 | 580 | 53.7 | 22.1 | 33.2 |

Note:
LHSV = liquid hourly space velocity of the educt or effluent - in ml. of educt or effluent per ml. of catalyst per hour $_3$—K$_2$CO$_3$Cr$_2$O$_3$—Co$_3$O$_4$—cement (46.3:26.2:2.5:5.0:20 percent) with different contact times. The results were shown in Table 4.

Table 4

| Contact time, Seconds | Conversion, % | Selectivity, % | |
|---|---|---|---|
| | | Indole | o-aminostyrene |
| 2.7 | 35.6 | 31.8 | 63.0 |
| 5.4 | 40.1 | 35.2 | 51.4 |
| 8.1 | 46.5 | 41.0 | 43.2 | various reaction conditions according to the table. After an operating period of 195 hours, the original conditions were returned to and the same conversion and selectivities in regards to indole and o-aminostyrene as at the beginning of the experimental series were obtained. It is clear from Table 8 that the catalysts of this invention do not require any regeneration period. A series of tests were also run using another type of catalyst of this invention.

Table 8

| Catalyst | Temperature, °C. | Contact Time, Seconds | Molar Ratio of Water to o-Ethyl-aniline | Elapsed Time, In Hours | Conversion, % | Selectivity | |
|---|---|---|---|---|---|---|---|
| | | | | | | Indole | o-aminostyrene |
| Copper chromite saturated with BaO | 582 | 2.3 | 13:1 | 43 | 32.4 | 39.9 | 44.7 |
| | 590 | 5 | 15:1 | 96 | 57.4 | 61.0 | 20.8 |
| | 570 | 5 | 15:1 | 103 | 43.3 | 49.1 | 36.1 |
| | 590 | 10 | 15:1 | 126 | 74.6 | 70.1 | 9.9 |
| | 590 | 10 | 10:1 | 188 | 64.1 | 69.2 | 15.1 |
| | 584 | 2.3 | 13:1 | 195 | 36.8 | 44.8 | 42.2 |
| Fe$_2$O$_3$—K$_2$CO$_3$—Cr$_2$O$_3$—Co$_3$O$_4$ -cement | 567 | 5.4 | 15:1 | 22 | 40.1 | 35.2 | 51.4 |
| | 580 | 2.7 | 15:1 | 30 | 41.1 | 41.0 | 50.7 |
| | 584 | 2.7 | 10:1 | 46 | 40.3 | 38.3 | 49.2 |
| | 600 | 1.4 | 15:1 | 70 | 44.4 | 43.2 | 48.6 |

EXAMPLE 5 o-Ethylaniline was passed at a liquid hourly space velocity of 0.75 per hour over a catalyst (copper chromite activated with BaO) at 660°C and at various pressures. The results obtained are shown in Table 5.

Table 5

| Pressure, Torr | Conversion, % | Selectivity, % | |
|---|---|---|---|
| | | Indole | o-aminostyrene |
| 16 | 81 | 42.5 | 10.6 |
| 710 | 97 | 25.8 | 4.5 |

EXAMPLE 6 o-Ethylaniline and water were reacted using a Fe$_2$O$_3$—K$_2$CO$_3$—Cr$_2$O$_3$—CuO—cement (43.9:25:2.5:4.8:23.9 percent) catalyst at a temperature of 607°C and using a contact time of one second. The molar ratio of water to o-ethylaniline was varied and the results are reported in Table 6.

Table 6

| Molar Ratio of Water to o-ethylaniline | Conversion, % | Selectivity, % | |
|---|---|---|---|
| | | Indole | o-aminostyrene |
| 10:1 | 41.2 | 42.2 | 46.2 |
| 15:1 | 44.1 | 47.7 | 43.5 |
| 25:1 | 56 | 50.6 | 33.8 |

EXAMPLE 7 o-Ethylaniline and water at a molar ratio of 1:15 was reacted at 600°C using the catalyst according to Example 4 and using a contact time of 1.4 seconds. The conversion amounted to 44.4 percent, the selectivity of indole amounted to 43.2 percent and the selectivity of aminostyrene amounted to 48.6 percent.

EXAMPLE 8 o-Ethylaniline and water were reacted using copper chromite activated with BaO type of catalyst under

EXAMPLE 9

A mixture of water and the following compounds:

| o-ethylaniline | 60 percent |
|---|---|
| o-aminostyrene | 36.5 percent |
| indole | 2.9 percent | was reacted at a molar ratio of 15:1 at 600°C using the catalyst of Example 4, and using a contact time of 1.3 seconds. The conversion was 29 percent, and the selectivity of indole amounted to 95.4 percent.

EXAMPLE 10

A mixture of water and the following compounds:

| p-ethylaniline | 79.2 percent |
|---|---|
| o-aminostyrene | 18.9 percent |
| indole | 0.4 percent | was reacted at a weight ratio of 2.23:1 at 600°C using the catalyst of Example 6 and using a contact time of 1.0 seconds. The conversion was 28.6 percent, the selectivity of indole amounted to 84.3 percent and the selectivity of o-aminostyrene amounted to 6.0 percent.

EXAMPLE 11

A mixture of water and the following compounds:

| o-ethylaniline | 77.16 percent |
|---|---|
| o-aminostyrene | 17.8 percent |
| indole | 0.7 percent | was reacted at a weight ratio of 2.53:1 at 590°C using an iron oxide catalyst and using a contact time of 0.7 seconds. The conversion amounted to 25.3 percent, the selectivity of indole was 45.5 percent and the selectivity of o-aminostyrene was 45.5 percent.

EXAMPLE 12

A mixture of water and the following compounds:

| | |
|---|---|
| o-ethylaniline | 84.7 percent |
| o-aminostyrene | 12.7 percent |
| indole | 0.6 percent | was reacted in a weight ratio of 1.5:1 at 590°C using a catalyst which was copper chromite activated with barium oxide and using a contact time of 5.0 seconds. The conversion amounted to 39.1 percent and the selectivity of indole was 85.3 percent. No apparent change in the amount of o-aminostyrene was found.

What is claimed is:

1. A process for the production of indole by catalytic dehydrocyclization which comprises, without the addition of free oxygen or gas containing free oxygen or combination thereof, reacting o-ethylaniline or o-aminostyrene or a mixture thereof with steam in the presence of a catalyst containing (i) at least one alkali metal oxide, carbonate or hydroxide, (ii) at least one component selected from the group consisting of $Cr_2O_3$, $V_2O_5$, $Co_3O_4$, $CuO$, $Fe_2O_3$, $Al_2O_3$, $ZnO$, $BaCrO_4$, $TiO_2$, $ZrO_2$, copper chromite activated and stabilized with barium oxide, $K_2CO_3$ activated with iron oxide and mixtures thereof, (iii) at least one alkaline earth metal oxide, carbonate or hydroxide or admixture of (i) to (iii) or any two of (i), (ii) and (iii), said reaction being conducted at a temperature between 500° and 700°C., and at a pressure between 10 mm Hg and 10 atmospheres, and the molar ratio of said steam to said o-ethylaniline or said o-aminostyrene or a mixture thereof is between 3 to 1 and 75 to 1, and separating out the resultant indole.

2. A process as described in claim 1 wherein the catalyst is used in a stationary bed.

3. A process as described in claim 1 wherein the catalyst is used in a moving bed.

4. A process as described in claim 1 wherein the catalyst is used in a fluidized bed.

5. A process as described in claim 1 wherein the reaction is conducted at a temperature between 550° and 650°C.

6. A process as described in claim 1 wherein the reaction is conducted at atmospheric pressure.

7. A process as described in claim 1 wherein the apparent contact time between the catalyst and the reactants is between 0.1 and 60 seconds.

8. A process as described in claim 1 wherein the apparent contact time between the reactants and the catalyst is between 0.5 and 30 seconds.

9. A process as described in claim 1 wherein an inert diluent is present during said reaction.

10. A process as described in claim 9 wherein said inert diluent is nitrogen.

11. A process as described in claim 9 wherein said inert diluent is argon.

12. A process as described in claim 9 wherein said inert diluent is carbon dioxide.

13. A process as described in claim 1 wherein any unconverted aminostyrene feed and aminostyrene formed during said reaction separated from said indole is fed into said reaction.

14. A process as described in claim 13 where said separation is achieved by distillation.

15. A process as described in claim 1 wherein said reaction is started with o-ethylaniline and aminostyrene, thereafter fresh o-ethylaniline being fed continuously to said reaction, and the unreacted o-ethylaniline and the o-aminostyrene formed during the reaction being separated from the resultant indole and being recycled to said reaction.

16. A process as described in claim 1 wherein said catalyst is copper chromite activated with barium oxide.

17. A process as described in claim 1 wherein said catalyst is zinc chromite activated with barium oxide.

18. A process as described in claim 1 wherein said catalyst is $Fe_2O_3$—$K_2CO_3$—$Cr_2O_3$—$Co_3O_4$ (46.3:26.2:2.5:5.0:20 percent).

19. A process as described in claim 1 wherein said catalyst is $Fe_2O_3$—$K_2CO_3$—$Cr_2O_3$—$CuO$—cement (43.9:25:2.5:4.8:23.0 percent).

20. A process as described in claim 1 wherein said catalyst is an alkali metal oxide, carbonate or hydroxide, said alkali metal being lithium, sodium, potassium, Rb, Cs or Fr.

21. A process as described in claim 1 wherein said catalyst is an alkaline earth metal oxide, carbonate or hydroxide, said alkaline earth metal being Be, Mg, calcium, Sr, barium or Ra.

22. A process as described in claim 1 wherein said catalyst is: $Fe_2O_3$—$K_2CO_3$—$Cr_2O_3$—$V_2O_5$(74.5:20:2:3.5 percent); $Cr_2O_3$—$Al_2O_3$—KOH (19:79:2 percent); $Cr_2O_3$—$K_2CO_3$(93.7 percent); $ZnO$—$Cr_2O_3$—$BaCrO_4$— Portland cement (35.8:29.0:17.7:17.5 percent); $TiO_2$—$Cr_2O_3$—$K_2CO_3$ (80:4:16); $TiO_2$—$Cr_2O_3$—$V_2O_5$—$Cr_2O_3$ (76.4:16.8:2.6:4.2 percent); ($ZrO_2$—$Al_2O_3$)—BaO (95.5); ($ZrO_2$—$Al_2O_3$)—$K_2CO_3$—KOH (90:9:1 percent); or $K_2CO_3$ activated with iron oxide which contains K compounds.

23. A process for the production of indole by catalyst dehydrocylization which comprises, without the addition of free oxygen or a gas containing free oxygen or combination thereof, reacting o-ethylaniline and o-aminostyrene with steam in the presence of a catalyst containing (i) at least one alkali metal oxide, carbonate or hydroxide, (ii) at least one alkaline earth metal oxide, carbonate or hydroxide, or (iii) admixture of (i) and (ii), said reaction being conducted at a temperature between 500° and 700°C., and at a pressure between 10 mm Hg and 10 atmospheres, and the molar ratio of said steam to said mixture of said o-ethylaniline is between 3 to 1 and 75 to 1, separating out the resultant indole, feeding, after said reaction is started, fresh o-ethylanniline continuously to said reaction, separating the unreacted o-ethylaniline and the o-aminostyrene formed during the reaction from the resultant indole by distillation, and recycling such to said reaction.

24. A process as described in claim 23 wherein the catalyst is used in a fluidized bed.

25. A process as described in claim 23 wherein the reaction is conducted at a temperature between 550° and 650°C.

26. A process as described in claim 23 wherein the apparent contact time between the catalyst and the reactants is between 0.1 and 60 seconds.

27. A process as described in claim 23 wherein the apparent contact time between the reactants and the catalyst is between 0.5 and 30 seconds.

28. A process as described in claim 23 wherein an inert diluent is present during said reaction.

29. A process as described in claim 28 wherein said inert diluent is n-pentane, isopentane, n-hexane, n-heptane, nitrogen argon or carbon dioxide.

30. A process as described in claim 23 wherein said catalyst is copper chromite activated with barium oxide.

31. A process as described in claim 23 wherein said catalyst is zinc chromite activated with barium oxide.

32. A process as described in claim 23 wherein said catalyst is an alkali metal oxide, carbonate or hydroxide, said alkali metal being lithium, sodium, potassium, Rb, Cs or Fr, or is an alkaline earth metal oxide, carbonate or hydroxide, said alkaline earth metal being Be, Mg, calcium, Sr, barium or Ra.

33. A process for the production of indole by catalystic dehydrocylcization which consists of, without the addition of free oxygen or a gas containing free oxygen or combination thereof, reacting a mixture of o-ethylaniline and o-aminostyrene with steam in the presence of an inert diluent and a catalyst containing (i) at least one alkali metal oxide, carbonate or hydroxide, (ii) at least one alkaline earth metal oxide, carbonate or hydroxide, (iii) at least one component selected from the group consisting of $Cr_2O_3$, $V_2O_5$, $Co_3O_4$, CuO, $Fe_2O_3$, $Al_2O_3$, ZnO, $BaCrO_4$, $TiO_2$, $ZrO_2$, copper chromite activated and stabilized with barium oxdie, $K_2CO_3$ activated with iron oxide, and mixtures thereof, or (v) admixture of (i) to (iii) or any two of (i), (ii) and (iii), said reaction being conducted at a temperature between between 500° and 700°C., and at a pressure between 10 mm Hg and 10 atmospheres, and the molar ratio of said steam to said o-ethylaniline or said o-aminostyrene or a mixture thereof is between 3 to 1 and 75 to 1, separating out the resultant indole, feeding, after said reaction is started, fresh o-ethylaniline continuously to said reaction, separating the unreacted o-ethylaniline and the o-aminostyrene formed during the reaction from the resultant indole by distillation, and recycling such to said reaction.

34. A process as described in claim 33 wherein the catalyst is used in a fluidized bed.

35. A process as described in claim 33 wherein the reaction is conducted at a temperature between 550° and 650°C.

36. A process as described in claim 23 wherein the apparent contact time between the catalyst and the reactants is between 0.1 and 60 seconds.

37. A process as described in claim 33 wherein said inert diluent is n-pentane, isopentane, n-hexane, n-heptane, nitrogen, argon or carbon dioxide.

38. A process as described in claim 33 wherein said catalyst is an alkali metal oxide, carbonate or hydroxide, said alkali metal being lithium, sodium, potassium, Rb, Cs or Fr, or an alkaline earth metal oxide, carbonate or hydroxide, said alkaline earth metal being Be, Mg, calcium, Sr. barium or Ra.

39. A process as described in claim 9 wherein said inert diluent is n-pentane, isopentane, n-hexane or n-heptane.

* * * * *